United States Patent
Boudreau, Sr.

(10) Patent No.: US 8,669,386 B2
(45) Date of Patent: Mar. 11, 2014

(54) ORGANIC TUNGSTEN COMPLEXES

(75) Inventor: David Boudreau, Sr., Ansonia, CT (US)

(73) Assignee: Vandebilt Chemicals, LLC, Norwalk, CT (US)

( * ) Notice: Subject to any disclaimer, the term of this patent is extended or adjusted under 35 U.S.C. 154(b) by 223 days.

(21) Appl. No.: 13/412,834

(22) Filed: Mar. 6, 2012

(65) Prior Publication Data

US 2012/0165563 A1 Jun. 28, 2012

Related U.S. Application Data

(63) Continuation-in-part of application No. 12/052,390, filed on Mar. 20, 2008, now abandoned.

(60) Provisional application No. 61/563,204, filed on Nov. 23, 2011, provisional application No. 60/895,792, filed on Mar. 20, 2007.

(51) Int. Cl.
- *C07F 11/00* (2006.01)
- *C10M 159/18* (2006.01)
- *C10M 101/00* (2006.01)

(52) U.S. Cl.
CPC ............... *C07F 11/005* (2013.01); *C10M 1/08* (2013.01); *C10N 2210/06* (2013.01)
USPC .................. 556/61; 556/57; 556/63; 508/367

(58) Field of Classification Search
CPC ..... C07F 11/005; C10N 2210/06; C10M 1/08
USPC ................................ 556/61, 63, 57; 508/367
See application file for complete search history.

(56) References Cited

U.S. PATENT DOCUMENTS

| | | | |
|---|---|---|---|
| 3,290,245 A | 12/1966 | Elliot et al. | |
| 4,889,647 A | 12/1989 | Rowan et al. | |
| 6,096,693 A | 8/2000 | Nakanishi et al. | |
| 2004/0214731 A1 | 10/2004 | Tynik | |
| 2007/0042917 A1 | 2/2007 | Ravichandran et al. | |
| 2008/0234154 A1 | 9/2008 | Boudreau | |
| 2009/0029888 A1 | 1/2009 | Ravichandran et al. | |

OTHER PUBLICATIONS

Thnman Taylor, The Annominum Tungstate, John Harrison Lab of Chemistry, No. 64: Mar. 12, 1902, pp. 1-15.
International Search Report Dated Dec. 12, 2012, Mailed Jan. 23, 2013.
Boudreau, D., 312 Declaration date Jun. 22, 2010.

*Primary Examiner* — Porfirio Nazario Gonzalez
(74) *Attorney, Agent, or Firm* — Norris McLaughlin & Marcus P.A.

(57) ABSTRACT

This invention relates to an organic tungsten complex prepared by providing a strongly acidic tungsten precursor having $pH \leq 2.5$, and either reacting the tungsten precursor with a nitrogenous base to form a tungsten salt intermediate having a pH ranging from $\geq 5$ to $\leq 8.5$, and further reacting the tungsten salt intermediate with a fatty acid derivative of an alcohol, wherein the fatty acid derivative of an alcohol contains at least one free hydroxyl group; or reacting the tungsten precursor with a fatty acid derivative of an alcohol, wherein the fatty acid derivative of an alcohol contains at least one free hydroxyl group and a nitrogenous base. Further, this invention relates to lubricating compositions containing the inventive tungsten complexes.

18 Claims, No Drawings

ORGANIC TUNGSTEN COMPLEXES

RELATED APPLICATIONS

This application is a non-provisional of Ser. No. 61/563,204 filed Nov. 23, 2011, and is a continuation-in-part of Ser. No. 12/052,390 filed Mar. 20, 2008, which in turn is a non-provisional of application No. 60/895,792 filed Mar. 20, 2007.

FIELD OF THE INVENTION

The present invention relates to lubricant compositions imparting improved antiwear, corrosion, and antioxidancy properties. These compositions contain an organic tungsten complex which is defined as the reaction product of a fatty acid derivative of an alcohol and a tungsten salt.

BACKGROUND OF THE INVENTION

Zinc dialkyldithiophosphates (ZDDP) have been added to lubricant compositions for decades due to their low cost, and ability to act as a multifunctional additive-possessing antiwear, and antioxidant properties. Despite the great benefit of these materials, it is well known that the sulfur and phosphorus from these compounds volatilize and pass through the exhaust systems of internal combustion engines where they inevitably poison catalytic converters.

One method to minimize the amount of sulfur and phosphorus reaching the catalytic converter is to reduce the amount of ZDDP present in the lubricant composition. In doing so, it is necessary to increase the amount of other additives to compensate for the antioxidant and antiwear functionality lost by the decrease or removal of ZDDP.

There are a multitude of examples in the patent literature where ZDDP concentrations are either reduced or eliminated. In these examples, the term "low phosphorus" is often used, but as this is a relative term, it may include phosphorus levels as high as 1000 ppm P. Therefore it is necessary in the following discussion to define a "low phosphorus" composition as any lubricant composition containing a phosphorus level below 600 ppm P. This is a minimum performance standard requirement, as set for an ILSAC GF-4 passenger car motor oil. The terms "zero phosphorus", "no phosphorus", or "phosphorus free" are defined herein as phosphorus concentrations less than or equal to 10 ppm P.

For the purpose of this discussion, a "low sulfur" composition is defined as any lubricant composition containing a sulfur level below 500 ppm S. This is defined as the minimum sulfur content required of an ILSAC GF-4 SAE 0W or SAE 5W grade motor oil.

Zero phosphorus lubricant formulations which maintain an acceptable level of wear have been demonstrated through the addition of a complex blend of phosphorus free antiwear additives, ashless friction reducers, extreme pressure additives, antioxidants, detergents and polymeric viscosity modifiers and flow improvers, as exemplified in U.S. Pat. Nos. 5,346,635, and 5,439,605. These examples are not low sulfur formulations, as defined above.

Low phosphorus or zero phosphorus lubricant formulations having acceptable wear have been demonstrated with the addition of detergents, as exemplified in U.S. Pat. Nos. 6,159,911, 6,784,143, and U.S. Pat. App. No. 2007/0049507. These examples are not low sulfur formulations, as defined above.

Low phosphorus lubricant formulations having acceptable wear have been demonstrated with the addition of an organo-molybdenum dithiocarbamate compound, as exemplified in U.S. Pat. Nos. 6,500,786, and 6,852,679. These are not low sulfur formulations, as defined above.

Low phosphorus lubricant formulations having acceptable wear have been demonstrated with the addition of ashless compounds, such as sulfurized olefins (U.S. Pat. Nos. 4,330,420, and 6,884,855) and dithiocarbamates (U.S. Pat. Nos. 4,758,362, 6,852,680, and 7,160,845). These are not low sulfur formulations, as defined above.

Low phosphorus lubricant formulations having acceptable wear have been demonstrated using borated succinimide dispersants, as exemplified by U.S. Pat. No. 7,122,508. These are not low sulfur formulations, as defined above.

A zero phosphorous, low sulfur lubricant composition and method of use is described in U.S. Pat. No. 6,588,393 where a continuously fresh stream of lubricant is added to a running engine and the equivalent amount of used oil is removed and combined with the fuel stream. This is a unique system designed to reduce NOx emissions. Properties, such as wear, and friction are not considered.

It has now been discovered that a phosphorus and sulfur free organic tungsten complex may be employed in a lubricant composition containing no phosphorus and no sulfur. The organotungstate provides excellent antiwear and limits oxidation and corrosion. The organotungstate also proves effective in lubricant compositions where phosphorus and sulfur are present.

The patent literature contains several examples of tungsten being used in lubricant compositions. For instance, the use of ammonium tungstate salts, also referred to as oxytungstate salts, in aqueous environments is known. In particular, U.S. Pat. Nos. 4,626,367, and 4,816,303, and European Patent No. 2,044,186 disclose how simple alkali earth tungsten salts may be employed as aqueous corrosion inhibitors. Tungstate salts have also been used as antioxidants in aqueous tin electroplating systems, as disclosed in U.S. Pat. Nos. 5,378,347, and 7,151,049.

Tungsten salts have been employed in nonaqueous base lubricant compositions as well. Simple inorganic salts of tungsten may be dispersed in grease and oil compositions, to be used as corrosion inhibitors, as exemplified in U.S. Pat. Nos. 6,010,984, 6,010,985, 6,017,857, 6,316,392, 6,331,509, 6,534,450, 6,632,781, 6,737,387, 6,858,160, and 7,265,080.

Oil and grease soluble tungstate salts have been prepared, most commonly through the incorporation of alkylammonium cations as exemplified in U.S. Pat. Nos. 4,298,485, 7,335,625, 7,858,565, 7,879,777, and 7,820,602 describe lubricant compositions containing alkylammonium polyoxotungstates as antioxidant agents. Further, U.S. Pat. Nos. 3,290,245 and 4,298,485 disclose the use of an oil soluble alkylammonium polyoxotungstate salt as a detergent and dispersant of cold sludge, and as a friction reducer when combined with a sulfur source (i.e. ZDDP).

U.S. Pat. No. 2,795,549 discloses the potential use of oil soluble ammonium 4-t-butyl catechol vanadate and tungstate salts, as copper and lead corrosion inhibitors. More complex salts of tungsten may also be employed in lubricant compositions, such as the polycarboxylate salts of U.S. Pat. Nos. 5,321,146, 5,641,472, and 5,629,435. The tungsten complexes used in the lubricating composition of this invention are not tungstate salts, and are therefore not analogous to tungstate salts.

There are several references in the patent literature to other organotungsten compounds being used in lubricant compositions, which are not tungstate salts. For example, tungsten carboxylates such as that claimed, but not taught, in U.S. Pat. No. 4,824,611, could be employed in non-aqueous lubricant systems. U.S. Pat. No. 3,234,129 discloses a lubricating composition containing either an oil soluble diarene tungsten tricarbonyl, arene tungsten, or a dichlorotetranaphthyloxy tungsten which is effective as an antiwear additive, but only when combined with ZDDP. U.S. Pat. No. 6,211,123 describes the use of an oil soluble trinuclear thiotungstate for antiwear, antioxidant and friction control in a lubricant composition. U.S. Pat. Nos. 4,529,526, and 4,171,558 claim lubricating composition containing a zinc, molybdenum or tungsten dialkyldithiophosphate as antiwear agents, but only teach zinc and molybdenum. U.S. Pat. Nos. 3,068,259 and 3,193,500 described an extreme pressure lubricant containing a tungsten dialkyldithiophosphate which must be prepared from tungsten pentachloride.

Tungsten dithiocarbamates and their use in lubricant compositions are also known. U.S. Pat. No. 4,846,983 declares the synthesis of a tungsten dithiocarbamate from WO3 but contains neither data confirming that the complex was formed, nor does it exemplify a lubricant composition containing the organic tungsten complex according to an embodiment of the present invention. Other preparations of tungsten dithiocarbamates, such as those in U.S. Pat. Nos. 5,308,519, and 6,211, 123 and World Patent Application WO2004/043910, teach the synthesis of various tungstates by either the use of expensive starting materials and reagents, or by producing tungsten dithiocarbamates in yields which are not viable on a commercial scale.

It has now been unexpectedly discovered that a phosphorus and sulfur free organic tungsten complex according to embodiments of the present invention imparts antiwear, corrosion, and antioxidancy properties upon a lubricating composition. These characteristics are maintained even in lubricant compositions containing reduced phosphorus and sulfur levels.

SUMMARY OF THE INVENTION

One embodiment of the present invention relates to an organic tungsten complex prepared by reacting a tungsten salt and a fatty acid derivative of an alcohol, wherein the tungsten salt is the reaction product of a strongly acidic tungsten and a nitrogenous base. The alcohol may be either a monoglyceride, diglyceride, and/or a fatty amide, and the resulting fatty derivative must have at least one free hydroxyl group. The present invention also relates to lubricant compositions having improved antiwear, corrosion, and antioxidancy properties, in which the lubricant compositions contain said organic tungsten complex. In one aspect of this invention, a sulfur and phosphorus free organic tungsten complex is contained in a lubricating composition, and imparts improved antiwear performance on the lubrication composition, even when said composition contains low to no levels of phosphorus and low to no levels of sulfur.

In another aspect of this invention, a sulfur and phosphorus free organic tungsten complex is contained in a lubricating composition along with a zinc dialkyldithiophosphate (ZDDP). The combination of the organic tungsten complex with ZDDP is synergistic, providing significantly higher antiwear activity than either of the components when used separately in lubricants.

In yet another aspect of this invention, a sulfur and phosphorus free organic tungsten complex is contained in a lubricating composition along with an aminic based antioxidant, such as an alkylated diphenylamine. The combination of the organic tungsten complex with the antioxidant is synergistic, providing significantly higher antioxidant activity than either of the components when used separately in lubricants.

The present invention further relates to a sulfur and phosphorus free organic tungsten complex is contained in a lubricating composition and consequently increasing the corrosion resistance of the lubrication composition. A lubricating composition may contain, in addition to the organic tungsten complex: an alkylated diphenylamine, secondary diarylamine and/or an N-alkylated diphenylamine, at about 0.1 to 4.0 mass percent; a metal dialkyldithiophosphate, preferably zinc dialkydithiophosphate, in an amount of about 0.05 to 5.0 mass percent, preferably 0.1 to 1.0 mass percent.

DETAILED DESCRIPTION OF THE INVENTION

The present invention relates to a lubricating composition containing a majority component of a lubricating base and a minority component of an organic tungsten complex, preferably in concentration which provides about 10 to 3000 ppm W, more preferably about 10 to 1000 ppm W, and most preferably about 100 to 1000 ppm W. Lubricating bases to be used in the present invention include base oils for lubricating oils, which are composed of mineral oils, synthetic oils or mixtures thereof, and base greases in which a thickener is compounded in any of the base oils. Mineral oils may be paraffinic or naphthenic. Paraffinic oils may be Group I solvent refined base oils, Group II hydrocracked base oils, and Group III high viscosity index hydrocracked base oils. Synthetic oils may consist of Group IV polyalphaolefin (PAO) type, and Group V synthetic oils, which include diesters, polyol esters, polyalkylene glycols, alkyl benzenes, organic esters of phosphoric acids, and polysiloxanes.

The organic tungsten complex of this invention is the reaction product of (1) a fatty acid derivative of an alcohol, the fatty acid derivative containing at least one free hydroxyl group and (2) a tungsten salt intermediate at pH ranging from $\geq 5$ to $\leq 8.5$, wherein the tungsten salt intermediate is the reaction product of a strongly acidic tungsten precursor of pH$\leq 2.5$ and a nitrogenous base.

In particular the fatty acid derivative is a monoglyceride, diglyceride and/or a fatty amide. The fatty amide in turn, is the reaction product of a fatty acid, monoglyceride, diglyceride, or triglyceride with an ethanolamine. Methods for preparing the analogous organomolybdates are disclosed in U.S. Pat. Nos. 4,889,647, 5,137,647, 5,412,130, and 7,205,423; the disclosures of which are incorporated herein by reference in their entirety.

We have surprisingly found that the organotungstate complexes of this invention cannot be formed by following the disclosed methods used for preparing the analogous molybdenum complexes. Instead, the organotungstate complex of this invention can only be formed by carefully controlling the pH during two crucial processing steps. In particular, the ammonium tungstate intermediate must have a pH ranging from $\geq 5$ to $\leq 8.5$. Furthermore, in order to form the inventive organotungstate complex, the ammonium tungstate intermediate, in turn, can only be formed by using an acidic tungsten precursor having a pH of $\leq 2.5$.

The acidic tungsten precursor of pH$\leq 2.5$ may be obtained by a variety of methods. One method is the combination of a tungsten source and water, wherein that combination inherently produces an aqueous solution or suspension of pH$\leq 2.5$. Non-limiting examples of tungsten sources capable of producing aqueous solutions or suspensions of pH$\leq 2.5$ are oxides of tungsten such as tungsten oxide, tungstic acid, halides of tungsten such as $WCl_6$, $WOCl_4$, $WF_6$, and alkoxides of tungsten such as tungsten isopropoxide, and tungsten dichloro triethoxide.

The acidic tungsten precursor of pH≤2.5 may also be obtained by combination of a tungsten source and water, wherein that combination produces an aqueous solution or suspension of pH>2.5. Non-limiting examples of tungsten sources which produce an aqueous solution or suspension of pH>2.5 are orthotungstates, metatungstates, paratungstates, Group I salts of orthotungstates, metatungstates, and paratungstates, Group II salts of orthotungstates, metatungstates, and paratungstates, and ammonia based salts of orthotungstates, metatungstates, and paratungstates. To obtain the acidic tungsten precursor of pH≤2.5 from these tungsten sources, the pH of the solution or suspension is adjusted, by common methods, to a pH≥7, preferable pH≥8.5. The aqueous solution or suspension is then acidified to pH≤2.5 using a strong acid to obtain the acidic tungsten precursor of pH≤2.5. Non-limiting examples of useful strong acids, defined as those which are completely ionized in water in a solution of 1 molar or less to give one or more protons per acid molecule, include hydroiotic acid, hydrobromic acid, perchloric acid, hydrochloric acid, nitric acid, sulfuric acid, and toluenesulfonic acid.

The ammonium tungstate salt intermediate used in the process of this invention may be prepared by adjusting the acidic tungsten precursor of pH≤2.5 to achieve a pH of ≥5 to ≤8.5, with a nitrogenous base in a 1:0.5 to 1:2 molar ratio, preferably a 1:1 molar ratio. Preferably, the nitrogenous base is a basic amine. More preferably, the nitrogenous base is an alkyl amine, such as ethanolamine containing at least one amine group and at least one hydroxyl group.

The ammonium tungstate salt intermediate is then reacted with a fatty acid derivative containing at least one free hydroxyl group, such as an ethanolamide or glyceride, whereupon water and excess amine are driven from the reaction. The resulting organotungstate complexes possess distinctly different performance characteristics than organotungstate complexes formed by other means.

In specific cases, where the fatty acid derivative contains both a free hydroxyl group and nitrogenous base, i.e. primary, secondary, or tertiary amine, the organotungstate complex may be formed directly from a reaction of such fatty acid derivative and the acidic tungsten precursor. In particular, the ammonium tungstate salt intermediate may be formed in situ, as an ammonium tungstate salt of the fatty acid derivative, wherein the nitrogenous base of the fatty acid derivative also serves as the nitrogenous base for the reaction with the acidic tungsten precursor, thus eliminating the need for a separate step. Due to the complex composition of the product, a specific chemical structure cannot be assigned to the organic tungsten complex. For illustrative purposes, a possible component in the composition of the organic tungsten complex of this invention is presented below in Formula I. This depiction is presented as an aid and not intended to limit the composition of the material.

Formula I

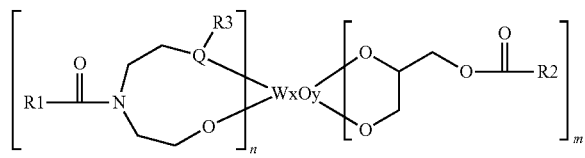

R1 and R2 may represent the same or different fatty oil residue. The preferred fatty oils are glyceryl esters of higher fatty acids containing at least 12 carbon atoms and may contain 22 carbon atoms and higher. Such esters are commonly known as vegetable and animal oils. Vegetable oils particularly useful are oils derived from coconut, corn, cottonseed, linseed, peanut, palm, soybean, rapeseed and sunflower seed. Similarly, animal fatty oils such as tallow may be used.

R3 may be hydrogen, C1 to C25 straight or branched chain alkyl radicals, C1 to C12 alkoxy-(C6 alkylene) radicals, C2 to C12 alkyl amino-(C2 to C6 alkylene) radicals. Q represents either nitrogen or oxygen. The sum of n+m is a value greater than or equal to 1; x is a value between 1 and 12 and y is a value greater than or equal to x.

The monoglycerides of this invention are readily described in U.S. Pat. Nos. 3,121,059, 4,765,918, 4,889,647, 5,137,647, 5,412,130, 6,500,974, 6,509,303, 6,528,463, 6,645,921, and 6,914,037. The disclosures of which are incorporated herein by reference in their entirety.

In many of these examples, and specifically in U.S. Pat. No. 4,889,647, the monoglyceride is prepared as a co-product of the reaction of a secondary amine with a fatty oil; whereupon the other major product being a fatty alkylamide. Additional reaction products consist of, but are not limited to, diglycerides and glycerol.

Certain fatty amides, being alcoholamides used in this invention, are readily described in U.S. Pat. Nos. 3,405,064, 4,765,918, 4,889,647, 5,137,647, 5,412,130, 6,057,283, 6,103,674, 6,509,303, 6,528,463, 6,645,921, 6,914,037. The disclosures of which are incorporated herein by reference in their entirety.

Specific examples of hydroxyamines useful in producing the alcoholamides of this invention are 2-(2-hydroxy-ethylamino)-ethanol, 2-[(2-aminoethyl)amino]ethanol, 2-({2-[(2-hydroxyethyl)amino]ethyl}amino)ethanol, 2-{[2-(methylamino)ethyl]amino}ethanol, 2-{[2-(diethylamino)ethyl]amino}ethanol, 2-(propylamino)ethanol, 2-[(3-aminopropyl)amino]ethanol, 2-[(2-amino-1,1-dimethylethyl)amino]ethanol, 2-(butylamino)ethanol, 2-(pentylamino)ethanol, 2-[(2-methylbutyl)amino]ethanol, 2-(isopentylamino)ethanol, 2-[(2-amino-2-methylpropyl)amino]ethanol, 3-[(2-hydroxyethyl)amino]-1-propanol, 2-[(1-methyloctyl)amino]ethanol, 2-(octadecylamino)ethanol, 2-(cyclohexylamino)ethanol, 1-[(2-hydroxyethyl)amino]-2-propanol, Bis(2-hydroxypropyl)amine, 1-(isopropylamino)-2-methyl-2-propanol, N-Methyl-D-glutamine, Diisopropanolamine, N-Benzylethanolamine, 2-[2-amino-2-methylpropyl)amino]-2-methyl-1-propanol, 3-(methylamino)-1,2-propanediol, 1-[(2-aminoethyl)amino]-2-propanol, 2-[(3-{[2-hydroxy-1,1-bis(hydroxymethyl)ethyl]amino}propyl)amino]-2-(hydroxymethyl)-1,3-propanediol, 2-(octadecylamino)ethanol, 2-(isopropylamino)-1-butanol, 1-(undecylamino)-2-propanol, 2-[(2-{[1-(hydroxymethyl)-2-methylpropyl]amino}ethyl)amino]-3-methyl-1-butanol, 2-[(2-{[1-(hydroxymethyl)propyl]amino}ethyl)amino]-1-butanol dihydrochloride, (2R)-2-[(2-{[(1R)-1-(hydroxymethyl)propyl]amino}ethyl)amino]-1-butanol dihydrochloride, 1-(cyclohexylamino)-2-propanol, 2-[(1-adamantylmethyl)amino]ethanol hydrochloride, 1-deoxy-1-(methylamino)-glucitol, 1-deoxy-1-(methylamino)-galactitol, 2-pyrrolidinylmethanol, 2-(benzylamino)ethanol, 1-deoxy-1-(ethylamino)-glucitol, 3-pyrrolidinol, 2-piperidinylmethanol, 1-deoxy-1-(octylamino)-glucitol, 1-deoxy-1-(dodecylamino)-glucitol, 2-(benzylamino)-1-propanol.

The tungstate used for the preparation of the organic tungsten complex of this invention is an ammonium tungstate salt intermediate, which is the reaction product of an acidic tungsten precursor of pH≤2.5 and a nitrogenous base, giving a compound of the general formula:

$[(WO_3)_xO_yH_z][NR_5R_6R_7R_8]_{2y-z}$   Formula II

The ammonium tungstate salt intermediate of Formula II may be represented as a unique composition, where x is a finite value from 1 to 12. Additionally, x may represent a distribution of values in the range of 1 to 12. Consequently, the values of y and z will vary depending upon the value of x, and y will range from 1 to 20, preferably 1 to 5, and z will range from 0 to 20 with z≥y. The preparation of such compounds are well described in literature, as exemplified by Krause et al., Journal of the American Chemical Society, 47, pp. 1689-1694 (1925); Freedman, Journal of the American Chemical Society, 81, pp. 3834-3839 (1959); Keperl, "Isopolytungstates", Progress in Inorganic Chemistry, Vol. 4, Intersciences Press, New York (1962) p. 199; Comprehensive Inorganic Chemistry, Vol. 3, Bailar et al. eds., Pergamon Press Ltd., Oxford (1973) pp. 763-769; Filowitz et al. Inorganic Chemistry, 18, pp. 93-103 (1979); Errington et al., Journal of the Chemical Society: Chemical Communications, pp 649-651 (1993). Preparations are also described in U.S. Pat. Nos. 3,290,245, 4,278,642, 4,279,870, 4,298,485, 7,335,625, 7,820,602, US Publication No. 2008-0194440 A1 and World Patent Applications WO2004/094574 and WO2007/009022.

The tungsten precursor used to prepare the ammonium tungstate salt intermediates of Formula II is a hydrated oxide of tungsten having a pH≤2.5. Tungsten sources which may be used in the course of preparing the tungsten precursor of this invention include tungsten compounds in the +4, +5 or +6 oxidation state. Examples of these include, but are not limited to, the tungsten oxides of $WO_2$ and $WO_3$, tungstic acid ($H_2WO_4$) and metal salts thereof, such as $Li_2WO_4$, $Na_2WO_4 \cdot 2H_2O$, $K_2WO_4$, $Cs_2WO_4$, $MgWO_4$, $CaWO_4$, $SrWO_4$, $BaWO_4$, $BaCaWO_6$, $MnWO_4$, $CoWO_4$, $CuWO_4$, $Ag_2WO_4$, $ZnWO_4$, $CdWO_4$, $PbWO_4$, and $Bi_2(WO_4)_3$, ammonium tungstates such as $(NH_4)_2WO_4$, $(NH_4)_{10}[H_2W_{12}O_{42}]\cdot xH_2O$, and $(NH_4)_6H_2W_{12}O_{40} \cdot xH_2O$, halides of tungsten such as $WCl_4$ $WCl_6$, $WF_6$, and $WO_2Cl_2$, and organotungstates such as $W(CO)_6$, $W(OC_2H_5)_6$, $WCl_2(OC_2H_5)_3$, and $W[OCH(CH_3)_2]_6$. It would be understood by one skilled in the art that tungsten sources, which do not inherently produce an aqueous solution or suspension of pH≤2.5, may be converted to such, by known methods.

Perhaps the only limiting factor on the tungsten source used is cost and availability. Therefore, in this light, preferred tungstates which may be used as a source of tungsten in the preparation of the tungsten precursor of this invention are sodium tungstate, sodium metatungstate, sodium polytungstate, ammonium metatungstate, ammonium paratungstate, tungstic acid, tungsten(VI) oxide, calcium tungstate, and hydrates thereof.

Nitrogenous bases used in the preparation of the ammonium tungstate salt intermediate of this invention include monoamines of the general formula:

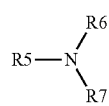

Formula III wherein R5, R6 and R7 are hydrogen; i.e. ammonia. The monoamine may also be a primary amine wherein R5 and R6 are hydrogen, and R7 represents linear, branched, saturated or unsaturated alkyl of 1 to 40 carbon atoms that may optionally contain at least one ether moiety, cycloalkyl of 5 to 40 carbon atoms, aryl of 6 to 40 carbon atoms, or aralkyl of 7 to 9 carbon atoms, where the aralkyl is substituted further by alkyl of 1 to 36 carbon atoms. Examples of primary amines useful to this invention are methylamine, isopropylamine, 2-aminoethanol, 3-isopropoxypropylamine, 2-ethylhexyloxypropylamine, Armeen® C (available from Akzo Nobel), Primene™ JM-T and Primene™ 81-R (available from Rohm & Hass).

The monoamine may also be a secondary amine, wherein R5 is hydrogen and R6 and R7 independently represent linear, branched, saturated or unsaturated alkyl of 1 to 40 carbon atoms that may optionally contain at least one ether moiety, cycloalkyl of 5 to 40 carbon atoms, aryl of 6 to 40 carbon atoms, or aralkyl of 7 to 9 carbon atoms, where the aralkyl is substituted further by alkyl of 1 to 36 carbon atoms.

The monoamine may be a tertiary amine, wherein R5, R6, and R7 independently represent a C1 to C36 residue that may optionally contain at least one ether moiety, cycloalkyl of 5 to 12 carbon atoms, or aralkyl of 7 to 9 carbon atoms, where the aralkyl is further substituted by alkyl of 1 to 36 carbon atoms.

The monoamine may be a quaternary amine of the formula:

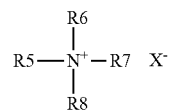

Formula IV wherein R5, R6, R7 and R8 are independently each a C1 to C36 residue that may optionally contain at least one ether moiety, cycloalkyl of 5 to 12 carbon atoms, or aralkyl of 7 to 9 carbon atoms, where the aralkyl is further substituted by alkyl of 1 to 36 carbon atoms. X represents a counter ion and may most commonly be chosen from the group of hydroxide, sulfide, sulfate, hydrogensulfate, fluoride, chloride, bromide or iodide.

Nitrogenous bases used in the preparation of the ammonium tungstate salt intermediate of this invention may include a diamine of the general formula:

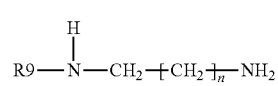

Formula V wherein n is 1 to 5 and preferably 1 or 2, and R9 is a hydrocarbon-containing group containing a minimum of about 6 carbon atoms. R9 can be aliphatic or aromatic. In a preferred embodiment, R9 can be represented by the structure X2-O—X1-, wherein X1 is an alky chain of 2 or 3 carbons, and X2 is an alkyl moiety having 3 to 30 carbon atoms, more preferably an alkyl moiety having 7 to 20 carbon atoms, and where X2 can be a straight or branched, saturated or partially unsaturated hydrocarbon chain.

Examples of some mono-substituted diamines according to Formula V that may be used include phenylaminopropylamine, hexylaminopropylamine, benzylaminopropylamine, octylaminopropylamine, octylaminoethylamine, dodecylaminopropylamine, dodecylaminoethylamine, hexadecylaminopropylamine, hexadecylaminoethylamine, octadecylaminopropylamine, octadecylaminoethylamine, isopropyloxypropyl-1,3-diaminopropane, octyloxypropyl-1,3-diaminopropane, decyloxypropyl-1,3-diaminopropane, isodecyloxypropyl-1,3-diaminopropane, dodecyloxypropyl-1,3-diaminopropane, tetradecyloxypropyl-1,3-diaminopropane, isodecyloxypropyl-1,3-diaminopropane, isododecyloxypropyl-1,3-diaminopropane, isotridecyloxypropyl-1,3-diaminopropane. Mono-substituted diamines derived from fatty acids may also be used. Examples include N-coco alkyl-1,3-propanediamine (Duomeen® C), N-tallow alkyl-1,3-propanediamine (Duomeen® T), and N-oleyl-1,3-propanediamine (Duomeen® O), all obtained from Akzo Nobel.

Nitrogenous bases used in the preparation of the ammonium tungstate salt intermediate of this invention may include a diamine of the general formula:

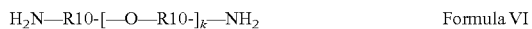

Formula VI wherein k is an integer from 1 to 10. R10 is a C1 to C6 hydrocarbon-containing group where most commonly R10 contains 2 to 3 carbons. Commercial polyetheramines of this type are available from Huntsman Chemical under the trade name Jeffamine®.

Nitrogenous bases used in the preparation of the ammonium tungstate salt intermediate of this invention may include a polyamine of the general formula:

Formula VI wherein k is an integer from 1 to 10. R10 is a C1 to C6 hydrocarbon-containing group where most commonly R10 contains 2 to 3 carbons. Commercial polyetheramines of this type are available from Huntsman Chemical under the trade name Jeffamine®.

Nitrogenous bases used in the preparation of the ammonium tungstate salt intermediate of this invention may include a polyamine of the general formula:

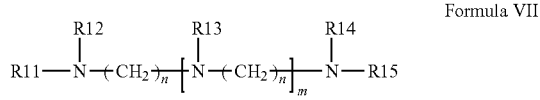

Formula VII wherein R11 thru R15 may be the same or different, and each may be hydrogen, C1 to C25 straight or branched chain alkyl radicals, C1 to C12 alkoxy-(C6 alkylene) radicals, C2 to C12 alkyl amino-(C2 to C6 alkylene) radicals; each n can be the same or different ranging from 2 to 6 and preferably ranging from 2 to 3 and m is a number from 0 to 10. Examples of such compounds according to Formula VII where m=0 are tetrabutoxy ethanediamine, tetrapropoxy ethanediamine, 1,4-Diazabicyclo[2.2.2]octane, 1,4-Dimethylpiperazine, N,N,N',N'-Tetramethylethylenediamine, N,N,N',N'-Tetraacetylethylenediamine, 1,1,4,7,10,10-Hexamethyltriethylenetetramine, N,N,N',N'-Tetrakis(2-hydroxyethyl)ethylenediamine, N,N,N',N'-Tetrakis(2-hydroxypropyl)ethylenediamine, ethylenediamine tetracetic acid and derivatives thereof. Examples of compounds where m is greater than 0 are diethylenetriamine, 4,7-Triazacyclononane, tris(2-aminoethyl)amine, tetraethylenepentamine, and pentaethylenehexamine.

Additionally, the sets of [R11, R12] and [R14, R15], may independently represent a cyclic structure, in particular a polyisobutylene succinimide. Examples of such polyamines are OLOA® 11000, OLOA® 11001, OLOA® 11002, (available from Chevron-Oronite), HiTEC® 644, and HiTEC® 646 (Afton Chemical).

Another class of polyamines applicable to this invention is the polyamine dispersant grafted viscosity index (VI) improvers. The patent literature is full of many examples of the preparation of such compounds. A sampling of these patents, which are hereby incorporated for reference, are U.S. Pat. Nos. 4,089,794, 4,171,273, 4,670,173, 4,517,104, 4,632,769, and 5,512,192. Typical preparation involves pre-grafting olefin copolymers with ethylenically unsaturated carboxylic acid materials to produce an acylated VI improver. The acyl groups are then reacted with polyamines to form carboxylic acid amides and succinimides.

Another class of polyamines applicable to this invention is the Mannich base dispersants. Typical Mannich bases which can be used in this invention are disclosed in U.S. Pat. Nos. 3,368,972, 3,539,663, 3,649,229, and 4,157,309. Mannich bases are typically prepared from alkylphenols having alkyl groups from 9 to 200 carbon atoms, and aldehydes, such as formaldehyde, and polyalkenylamine compounds, such triethylene tetramine, tetraethylene pentamine, and mixtures thereof.

Nitrogenous bases used in the preparation of the ammonium tungstate salt intermediate of this invention may be a triazole of the general formula:

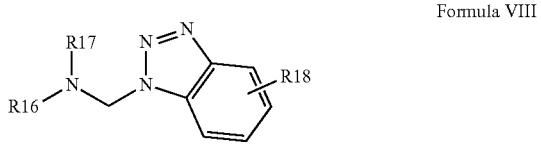

Formula VIII

R16 and R17 may be the same or different and may represent hydrogen, C1 to C20 alkyl, C3 to C20 alkenyl, C5 to C12 cycloalkyl, or C7 to C15 arylalkyl. R18 is a hydrogen or a C1 to C20 residue, preferably R18 may be represented by a 4- or 5-methyl radical.

Nitrogenous bases used in the preparation of the ammonium tungstate salt intermediate of this invention may be an imidazoline of the general formula:

Formula IX wherein X is a hydroxy or amino group and R19 is an alkyl group or fatty acid residue having 8 to 22 carbon atoms.

The organic tungsten complex of the present invention can be used in combination with other additives typically found in lubricating oil, as well as with other antiwear additives. Typical additives found in lubricating oils are dispersants, detergents, corrosion/rust inhibitors, antioxidants, e.g., secondary amine antioxidants, hindered phenolic antioxidants, sulfur-containing hindered phenolic antioxidants, sulfurized olefins, thiadiazoles, antiwear agents, e.g., zinc dialkyldithiophosphates, antifoamants, friction modifiers, seal swell agents, demulsifiers, VI improvers, and pour point depressants. See, for example, U.S. Pat. No. 5,498,809, incorporated herein by reference, for a description of useful lubricating oil composition additives.

Examples of dispersants include polyisobutylene succinimides, polyisobutylene succinate esters, Mannich Base ashless dispersants, and the like. Examples of detergents include metallic phenates, metallic sulfonates, metallic salicylates, and the like. Examples of friction modifiers that can be used in combination with the friction modifiers of the present invention include fatty acid esters and amides, organomolybdenum compounds, molybdenum dialkylthiocarbamates, molybdenum dialkyldithiophosphates, and the like. An example of an antifoamant is polysiloxane, and the like. An example of a rust inhibitor is polyoxyalkylene polyols, and the like. Examples of VI improvers include olefin copolymers and dispersant olefin copolymers, and the like. An example of a pour point depressant is poly(methyl methacrylate), and the like.

Examples of antioxidant additives that can be used in combination with the additives of the present invention include alkylated diphenylamines and N-alkylated phenylenediamines. Secondary diarylamines are well known antioxidants and there is no particular restriction on the type of secondary diarylamine that can be used in the practice of the present invention. The secondary diarylamine type of antioxidant in a lubricating oil provides a synergistic antioxidant mixture with the additive of the present invention. Preferably, the secondary diarylamine antioxidant is of the general formula R1-NH—R2, where R1 and R2 each independently represent a substituted or unsubstituted aryl group having 6 to 46 carbon atoms. Examples of some secondary diarylamines that can be employed in the practice of the present invention include: diphenylamine, dialkylated diphenylamine, trialkylated diphenylamine, or mixtures thereof, 3-hydroxydiphenylamine, 4-hydroxydiphenylamine, N-phenyl-1,2-phenylenediamine, N-phenyl-1,4-phenylenediamine, mono- and/or di-butyldiphenylamine, mono- and/or di-octyldiphenylamine, mono- and/or di-nonyldiphenylamine, phenyl-.alpha.-naphthylamine, phenyl-.beta.-naphthylamine, di-heptyldiphenylamine, mono- and/or di-(.alpha.-methylstyryl) diphenylamine, mono- and/or di-styryldiphenylamine, N,N'-diisopropyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-diphenyl-p-phenylenediamine, N,N'-di-(naphthyl-2)-p-phenylenediamine, N-isopropyl-N'-phenyl-p-phenylenediamine, N-(1,3-dimethylbutyl)-N'-phenyl-p-phenylenediamine, N-('-methylpentyl)-N'-phenyl-p-phenylenediamine, N-cyclohexyl-N'-phenyl-p-phenylenediamine, 4-(p-toluenesulfonamido) diphenylamine, 4-isopropoxydiphenylamine, tert-octylated N-phenyl-1-naphthylamino, and mixtures of mono- and dialkylated t-butyl-t-octyldiphenylamines.

Another example of the antioxidant types that can be used in combination with the additives of the present invention is the hindered phenolic type. The hindered phenolic type of antioxidant may provide a synergistic antioxidant mixture with the additives of the present invention in a lubricating oil. As illustrative of oil soluble phenolic compounds, may be listed alkylated monophenols, alkylated hydroquinones, hydroxylated thiodiphenyl ethers, alkylidenebis phenols, benzyl compounds, acylaminophenols, and esters and amides of hindered phenol-substituted alkanoic acids.

Another example of an antioxidant type that can be used in combination with the additives of the present invention includes oil soluble copper compounds, and the like.

Examples of antiwear additives that can be used in combination with the additives of the present invention include organoborates, organophosphites, organic sulfur-containing compounds, zinc dialkyldithiophosphates, zinc diaryldithiophosphates, phosphosulfurized hydrocarbon, and the like. The antiwear agents, in particular zinc dialkyldithiophosphates, provide a synergistic antiwear mixture with the additives of the present invention in a lubricating oil. Additionally, the antiwear agents, together with the secondary diarylamine type antioxidants in a lubricating oil provide a synergistic antioxidant mixture with the additives of the present invention. Suitable phosphates for use as antiwear agents include dihydrocarbyl dithiophosphates, wherein the hydrocarbyl groups contain an average of at least three carbon atoms. Particularly useful are metal salts of at least one dihydrocarbyl dithiophosphoric acid wherein the hydrocarbyl groups contain an average of at least three carbon atoms.

The metals useful to make the phosphate salts include Group I metals, Group II metals, aluminum, lead, tin, molybdenum, manganese, cobalt, and nickel. Zinc is the preferred metal. The preparation of metal phosphorodithioates is well known in the art and is described in a large number of issued patents, including U.S. Pat. Nos. 3,293,181, 3,397,145, 3,396,109, and 3,442,804, the disclosures of which are incorporated herein by reference in their entirety.

Also useful as antiwear additives are amine derivatives of dithiophosphoric acid compounds such as are described in U.S. Pat. No. 3,637,499, the disclosure of which is incorporated herein by reference in its entirety.

The reaction to prepare the organic tungsten complex is accomplished in essentially two phases, which may be performed with or without isolation of reaction intermediates. The first step involves preparation of a fatty acid derivative of an alcohol by functionalization of a fatty oil with a secondary alcoholamine, thus producing a fatty amide/glyceride mixture. The fatty amides and glycerides may also be prepared separately; where a fatty acid is reacted with a secondary alcoholamine, according to known methods, to produce the fatty amide; and where a triglyceride is hydrolyzed to a monoglyceride followed by purification as exemplified by, but not limited to U.S. Pat. Nos. 6,153,773 and 6,500,974.

The reaction between the fatty oil and secondary alcoholamine is typically carried out between 70 and 160° C., and preferably between 100 and 130° C. The reaction times may range from 1 to 8 hours, and are preferably 3 to 5 hours. A reaction solvent may be used as long as it does not react with the fatty oil or secondary alcoholamine. Preferred reaction solvents include toluene, xylenes, heptane, and various naphthenic, paraffinic and synthetic diluent oils. There is not particular limit on the volume of solvent used, but for practical purposes, a minimum volume is preferred.

The second phase involves the incorporation of tungsten through the addition of an ammonium tungstate salt intermediate to the fatty acid derivative (fatty alcoholamide, glyceride or fatty alcoholamide/glyceride mixture), and the subsequent removal of water and volatile organics from the reaction. These two reactants are presented in a molar ratio of one mole tungsten atoms (from the ammonium tungstate salt intermediate) to at least one mole of free hydroxyl group (from the fatty acid derivative). As an example, where the fatty acid derivative contains two free hydroxyl groups, the basic ratio is 1:0.5. The fatty acid derivative may be provided in excess of the minimum basic molar ratio in order to insure the completion of the reaction, preferably at least 3× the minimum up to about 10× minimum or greater, so as to complete the reaction, but without incurring undue waste. It is most preferable that the amine from the ammonium tungstate salt be removed from the reaction as a volatile organic, but this is not necessary.

It will be apparent to those skilled in the art that various modifications to reaction conditions, modifications of reagents, and combinations of reagents will achieve the organic tungsten complex of the present invention without departing from the spirit and scope of the present invention. Thus, it is intended that the present invention include modifications and variations that are within the scope of the appended claims and their equivalents.

EXAMPLES

The following examples are illustrative of the invention

Example 1

Sodium tungstate dihydrate tungsten source was solvated in a 20 molar excess of water giving a solution of pH=10.5. A 30.5% solution of sulfuric acid was added in 1:1 molar ratio, yielding a tungsten precursor as a pale yellow suspension of pH=1.3. From this tungsten precursor, an ammonium tungstate salt intermediate was prepared with the addition of triethylamine in a 1:1 molar ratio relative to tungsten. The reaction was stirred for 1 hour at 30° C. yielding a pasty white slurry of pH=8.4. Without isolation of the ammonium tungstate salt intermediate, a fatty acid ethanolamide was added in a molar ratio of 3.5:1. The ethanolamide was the reaction product of coconut oil and diethanol amine sold under the name of OD-896NT, available from R. T. Vanderbilt Co. Inc. The resulting emulsion was heated to 60° C. for 1 hour. Water and volatile organics were then removed by vacuum distillation as the temperature was raised to 130° C. The reaction was then held at temperature for a minimum of 2.5 hours under vacuum. It was then passed hot through filter media, yielding a dark brown oil containing 14.2%±0.5% tungsten as measured by ash content.

Example 2A

Intermediate

Fatty acid ethanolamide wherein Q=nitrogen and R3=hydrogen. Canola Oil and 2-[(2-aminoethyl)amino]ethanol were charged to a reaction flask in a 1:1.8 molar ratio. The reaction was placed under a nitrogen blanket and held at 120° C. for 3.5 hours. Product was a soft wax at room temperature.

Example 2

Sodium tungstate dihydrate was solvated in a 21 molar excess of water giving a solution of pH=10.4. A 30.5% solution of sulfuric acid was added in 1:1 molar ratio, yielding a pale yellow suspension of pH=1.4. Ethyldiisopropylamine was then added and the reaction stirred for 10 minutes at 40° C. pH=7.7. The product of Example 2A was then added in a 3.5:1 molar ratio relative to tungsten and the reaction refluxed for 3 hours. The temperature was raised to 130° C. while collecting distillate under vacuum. Product was then passed hot through filter media, yielding a clear brown oil. The product contained 10.3%±0.5% tungsten as measured by ash content.

Example A

Comparative

This is a comparative example to Example 1 in which acetic acid is used instead of sulfuric acid. Acidification of sodium tungstate led to a suspension of pH=5.8, above the requirement of the invention limit of 2.5. Triethylamine was then added in a 1:1 molar ratio relative to tungsten. This gave a pasty white slurry of pH=8.7. The remainder of the reaction was then run according to Example 1. Product was a pale yellow oil containing 0% tungsten as measured by ash content.

Example 3A

Intermediate

Fatty ethanolamide wherein Q=nitrogen and R3=hydrogen. Coconut oil and 2-[(2-aminoethyl)amino]ethanol were charged to a reaction flask in a 1:1.8 molar ratio. The reaction was placed under a nitrogen blanket and held at 120° C. for 4 hours. Product was a tan wax at room temperature.

Example 3

Sodium tungstate dihydrate was solvated in a 2.2 molar excess of water giving a solution of pH=10.5. A 30.5% solution of sulfuric acid was added in 1:1 molar ratio, yielding a pale yellow suspension of pH=1.3. Ethyldiisopropylamine was then added and the reaction stirred between 60° C. and 90° C. for 15 minutes; pH=7.8. The product of Example 3A was then added in a 6.5:1 molar ratio relative to tungsten, and heated to reflux, whereupon water and Ethyldiisopropylamine were collected. The reaction was then heated to 130° C. for 3 hours under vacuum to remove residual water and ethyldiisopropylamine. Product was then passed hot through filter media, yielding a clear brown oil which solidifies to a wax at room temperature. The product contained 7.9%±0.5% tungsten as measured by ash content.

Example 4

This Example is similar to Example 3 except that Example 3A intermediate is both the reactant and the amine source for the ammonium tungstate intermediate. Sodium tungstate dihydrate was solvated in a 60 molar excess of water giving a solution of pH=9.5. A 30.5% solution of sulfuric acid was added in 1:1 molar ratio, yielding a pale yellow suspension of pH=1.6. The product of Example 3A was then added in a 7:1 molar ratio relative to tungsten, and heated to 60° C., giving an ammonium tungstate salt of the fatty ethanolamide with a pH=8.0. Water was then removed by vacuum distillation as the temperature was raised to 130° C. The reaction was then held for 3 hours under vacuum. It was then passed hot through filter media, yielding a clear red-amber oil which solidifies to a wax at room temperature. The product contained 9.5%±0.5% tungsten as measured by ash content.

Example B

Comparative

This is a comparative example in which the ammonium tungstate intermediate is not in the correct pH range. Ammonium metatungstate was solvated in a 20 molar excess of water, giving a solution of pH=4.8, above the inventive limit of 2.5. The fatty acid ethanolamide of Example 3A was then added in a molar ratio of 6.5:1 relative to tungsten, giving a thick tan cream of pH=9, above the inventive limit of 8.5. The reaction was then heated to reflux and distillate collected. Vacuum was then applied to the system and the temperature allowed to rise to 130° C. The reaction was held at 130° C. under vacuum for 4 hours, then filtered hot through filter aid. The product was a dark brown wax at room temperature, and contained 10.1%±0.5% tungsten as measured by ash content.

Example C

Comparative

This is a comparative example where the fatty acid amide does not contain a free hydroxyl group. Coconut oil was combined in a 1:1.8 molar ratio with isodecyloxypropyl-1,3-diaminopropane (Available as Tomamine DA-14 from Air Products). The reaction was placed under a nitrogen blanket and held at 120° C. for 4.5 hours. Product was an amber oil.

Example D

Comparative

This is a comparative example. The fatty amide is not an ethanolamide. Sodium tungstate dihydrate was solvated in a 85 molar excess of water giving a solution of pH=10.3. A 30.5% solution of sulfuric acid was added in 1:1 molar ratio, yielding a pale yellow suspension of pH=1.4. The fatty amide of Example C was added, giving a light brown emulsion of pH=7.8. Distillate was collected as the reaction was raised to reflux and a vacuum slowly applied to the system. Once the majority of distillate was removed, the reaction was heated to 130° C. under vacuum for 4.5 hours. The product was then filtered hot through filter media, giving a dark red-amber oil which contained 6.8%%±0.5% tungsten as measured by ash content.

Example 5

Sodium tungstate dihydrate was solvated in a 20 molar excess of water giving a solution of pH=9.7. A 30.5% solution of sulfuric acid was added in 1:1 molar ratio, yielding a pale yellow suspension of pH=1.0. Ethyldiisopropylamine was then added in a 1:1 molar ratio relative to tungsten, giving a white emulsion of pH=8.4. Glycerol monooleate (Lonzest GMO, available from Lonza Inc.) was then added 10:1 molar ratio relative to tungsten. Toluene was also added to solvate the thick material. The temperature was raised to 92° C., whereupon the majority of the water and ethyldiiopropylamine were azeotroped off over 1 hour. The reaction was then raised to 130° C. for 1.5 hours while collecting residual aqueous azeotrop and returning toluene to the reaction. A vacuum was then slowly applied to the system at 130° C. and held for 2 hours while toluene was collected. The resulting product was filtered hot through filter media, giving a light amber oil containing 1.6%±0.5% tungsten as measured by ash content.

Example E

Comparative

This is a comparative example in which the ammonium tungstate intermediate is not in the correct pH range. Ammonium paratungstate was solvated in a 240 molar excess of water and heated to 60° C., giving a slurry of pH=5.8. No step was undertaken in order to lower the pH to below 2.5. Glycerol monooleate (Lonzest GMO, available from Lonza Inc.) was then added 120:1 molar ratio relative to tungsten. The pH remained at 5.8. Toluene was then added to the reaction and the procedure of Example 5 followed. Product was collected as a dark amber oil containing 0% tungsten as measured by ash content.

Example 6

An organic tungsten complex was prepared in a manner similar to Example 5 using triethylammonium tungstate and glyceryl monostearate (available as Lonzest® GMS from Lonza group Ltd). The molar ratio of glyceryl monostearate to tungsten was 2.9:1. The resulting product contained 2.2% tungsten, as measured by ash content.

Example 7

Oleic acid and diethanolamine were reacted in a 1:1 molar ratio to give an oleyldiethanolamide. Ethyldiisoproplyammonium tungstate was prepared by reacting sodium tungstate and sulfuric acid in a 1:1 molar ratio, with a resulting pH of 1.8. The resulting tungsten precursor and ethyldiisopropylamine were then reacted in a 1:1 molar ratio, with a resulting pH of 5.8. The oleyldiethanolamide and ammonium tungstate intermediate were then combined in a 3.5:1 molar ratio relative to tungsten. Removal of water and diethanolamide afforded a product containing 5.3% tungsten as measured by ash content.

Example 8

Rapeseed oil and diethanolamine were reacted in a 1:1.8 molar ratio yielding a fatty diethanolamide. Ethyldiisopropylammonium tungstate was prepared by reacting sodium tungstate and sulfuric acid in a 1:1 molar ratio, with a resulting pH of 1.9. The resulting tungsten precursor and ethyldiisopropylamine were then reacted in a 1:1 molar ratio, with a resulting pH of 5.8. The fattydiethanolamide and ammonium tungstate intermediate were then combined in a 3.5:1 molar ratio relative to tungsten. Removal of water and diethanolamide afforded a product containing 5.4% tungsten as measured by ash content.

Lubricating Composition M
ISO 32 Group II base oil, 600 ppm P from zinc dialkyldithiophosphate, 3% wt polyisobutylene succinimide dispersant, 0.5% wt alkylated diphenylamine antioxidant

Example F

Comparative

To lubricating composition M, is added 1.3% wt Example D.

Example 9

To lubricating composition M, is added 0.92% wt Example 4.

Example G

Comparative

To lubricating composition M, is added 0.87% wt Example B.

Example H

Comparative

To lubricating composition M is added 4.46% wt Glycerol monooleate (Lonzest GMO, available from Lonza Inc.). No tungsten complex is present.

Example 10

To lubricating composition M, is added 4.55% wt Example 5.

Example 11

To lubricating composition M, is added 4.55% wt Example 3.

Base Oil I

A commercially available mineral oil based lubricating composition meeting or exceeding API SM specifications (ExxonMobil SuperFlo®). This oil has a typical viscosity index of 137.

Example 12

Base Oil I was top treated with 700 ppm tungsten from Example 4.

Example 13

Base Oil I was top treated with 700 ppm tungsten from Example 2.

Base Oil J

A commercially available lubricating oil, composition meeting API SM specifications, and described by the manufacturer as a fully synthetic oil (ExxonMobil Mobil 1®). This oil has a typical viscosity index of 147.

Example 14

Base Oil J was top treated with 700 ppm tungsten from Example 4.

Example 15

Base Oil J was top treated with 700 ppm tungsten from Example 2.

Example K

Comparative

Base Oil I was top treated with 700 ppm tungsten from an oil soluble tungsten salt, available under the tradename VAN-LUBE® W 324 from R.T. Vanderbilt Company, Inc.

Example L

Comparative

Base Oil J was top treated with 700 ppm tungsten from an oil soluble tungsten salt, available under the tradename VAN-LUBE® W 324 from R.T. Vanderbilt Company, Inc.

The friction properties of comparative examples F, G and H, and inventive Examples 9 and 10, were measured on an SRV machine running a ball on disc at 50 Hz with a 1 mm stroke; 200N load; 140° C., for 1 hour. At the end of the test, wear volume was measured using a surface profilometer. See Table 1.

Antioxidancy of lubricants containing the inventive tungstates was determined by the Pressure Differential Scanning Calorimetry (PDSC) oxidation test (ASTM D6186 @ 210° C.). See Table 1

TABLE 1

| Example | ppm W | PDSC (minutes to induction) | CoF | Wear Volume μm³ |
|---|---|---|---|---|
| Lubricating Base M | | | | |
| Example H | 0 | 15 | 0.124 | 66281 |
| Example 9 | 700 | 17.7 | 0.108 | 24741 |
| Example 10 | 700 | 12.7 | 0.110 | 59163 |
| Example G | 700 | 5.2 | 0.125 | 469359 |
| Example F | 700 | 36.5 | 0.132 | 84083 |
| Base Oil I | | | | |
| Base Oil I | 0 | — | 0.121 | 34709 |
| Example 12 | 700 | — | 0.080 | 17087 |
| Example 13 | 700 | — | 0.059 | 12251 |
| Example K | 700 | — | 0.045 | 12016 |
| Base Oil J | | | | |
| Base Oil J | 0 | — | 0.106 | 43049 |
| Example 14 | 700 | — | 0.095 | 35285 |
| Example 15 | 700 | — | 0.090 | 38075 |
| Example L | 700 | — | 0.110 | 43747 |

In view of the above data, it is seen that the novel tungsten compounds of the invention are either comparable to, or exceed the performance of existing tungsten additives.

Performance properties were measured using an SRV machine using a ball on disc configuration, 1 mm stroke, 200N force, 50 Hz, 140° C. for 2 hours. At the end of the test, wear volume was measured using a surface profilometer. Results are shown in Table 2

TABLE 2

| | ppm W | | | | |
|---|---|---|---|---|---|
| | 0 | 10 | 100 | 700 | 1000 |
| Example 9 | 56314 | 44148 | 28811 | — | 21983 |
| Example 11 | 56314 | 28530 | 13750 | 27103 | — |

Performance properties were measured using an SRV machine using a ball on disc configuration, 1 mm stroke, 200N force, 50 Hz, 140° C. for 2 hours. The coefficient of friction at the end of the test is shown in Table 3

TABLE 3

| | ppm W | | | | |
|---|---|---|---|---|---|
| | 0 | 10 | 100 | 700 | 1000 |
| Example 9 | 0.142 | 0.136 | 0.126 | — | 0.111 |
| Example 11 | 0.128 | 0.127 | 0.106 | 0.115 | 0.106 |

The data shows that the performance characteristics of a lubricant containing an organotungsten complex of this invention are distinctly different than that found in lubricants using tungstates prepared via alternate methods. In particular, in comparative examples wherein the strict pH limitations of the invention are not followed during the processing steps, or the fatty acid derivative does not contain free hydroxyl groups, the results are clearly inferior. The coefficient of friction and wear volume of a lubricant composition containing an organotungstate complex of this invention are significantly improved over amine salt analogs prepared according to the prior art methods. Additionally, the antioxidancy benefit of compounds according to this invention are distinctly improved over their direct amine salt analogs.

Furthermore, though demonstrated by the superior performance data, it is also clear that the complexes prepared according to the specific process steps of the invention have a structure which is distinct from tungstate salts in general and is distinct from analogous compounds by standard methods known in the art. Without being restricted to theory, tungsten complexes containing W—O bonds show distinct absorptions in the infrared spectrum within the 629-990 cm$^{-1}$ wavenumber range, due to W—O bond stretching. [M. V. Nikanovich, V. A. Lastochkina, N. M. Ksenofontova, R. A. Puko and T. I. Razvina, *Interpretation of vibrational spectra of double tungstates KA$^{III}$(WO$_4$)$_2$ (A$^{III}$=Gd, Lu, Y)*, Journal of Applied Spectroscopy v50 n2 pp 175-178 (1989)]. Because, these absorptions are highly dependent upon environment, only very close analogs of tungstate salts and the tungsten complexes of this invention can be compared with any significant discernability by infrared absorption. Examples 3, 4, and B are all reaction products of parent fatty acid derivative Example 3A. Examples 3 and 4 are tungsten complexes of this invention and show characteristic W—O absorptions at 914 cm$^{-1}$, 868 cm$^{-1}$, and 828 cm$^{-1}$. Comparative Example B contains additional absorptions at 794 cm$^{-1}$ and 779 cm$^{-1}$ which are absorptions commonly associated with alkylammonium tungstate salts. [Peter J. S. Richardt, Robert W. Gable, Alan M. Bond, and Anthony G. Wedd, *Synthesis and Redox Characterization of the Polyoxo Anion, γ\*-[S$_2$W$_{18}$O$_{62}$]$^{4-}$: ▢A Unique Fast Oxidation Pathway Determines the Characteristic Reversible Electrochemical Behavior of Polyoxometalate Anions in Acidic Media*, Inorganic Chemistry v40 n4 pp 703-709 (2001); S. V. Chong, B. Ingham, J. L. Tallon, Novel materials based on organic-tungsten oxide hybrid systems I: synthesis and characterization, Current Applied Physics, v4, n2-4, pp 197-201 (2004)]. Therefore, as evidenced by the infra-red spectra, the W—O bonding structure of inventive Examples 3 and 4 are distinctly different than the bonding structure of the analogous tungstate salt.

Lastly, the monoglyceride tungsten complex used in Example 10 cannot be compared to an analogous complex made using accepted literature methods, such as those disclosed in U.S. Pat. Nos. 7,335,625, and 7,820,602, because these methods produce only amine salts of tungsten.

The above embodiments have shown various aspects of the present invention. It is to be understood that various modifications thereof will become apparent to those skilled in the art. Therefore it is to be understood that the invention disclosed herein is intended to cover such modifications as fall within the scope of the appended claims.

What is claimed is:

1. A process for preparing an organic tungsten complex, comprising the steps of, in order:
   (a) providing a strongly acidic tungsten precursor having pH≤2.5, and either
   (b)(i) (A) reacting the tungsten precursor with a nitrogenous base to form a tungsten salt intermediate having a pH ranging from ≥5 to ≤8.5, and
      (B) reacting the tungsten salt intermediate with a fatty acid derivative of an alcohol, the fatty acid derivative of an alcohol containing at least one free hydroxyl group; or
   (b)(ii) reacting the tungsten precursor with a fatty acid derivative of an alcohol, the fatty acid derivative of an alcohol containing at least one free hydroxyl group and a nitrogenous base.

2. The process of claim 1, wherein step (a) further comprises preparing the tungsten precursor by, in order:
   (i) selecting an aqueous tungsten source having pH>2.5, and
   (ii) adjusting the pH to ≤2.5.

3. The process of claim 2, wherein step (a) further comprises preparing the tungsten precursor by, in order:
   (i) selecting an aqueous tungsten source at pH>2.5
   (ii) (A) adjusting the pH of the tungsten source to pH≤7, and
      (B) combining with adjusted tungsten source with an acid to bring the pH of the tungsten source to ≤2.5.

4. The process of claim 3, wherein step (ii)(A) comprises adjusting the pH of the tungsten source to pH≥8.5.

5. The process of claim 1, wherein in step (b)(i)(A), the tungsten precursor is reacted with the nitrogenous base at a molar ratio of about 1:0.05 to about 1:2.

6. The process of claim 5, wherein the molar ratio is about 1:1.

7. The process of claim 6, wherein in step (b)(i)(B), the tungsten salt intermediate is reacted with the fatty acid derivative of an alcohol at a ratio of one mole tungsten atoms to at least one mole of free hydroxyl groups.

8. The process of claim 1, wherein the fatty acid derivative of an alcohol is chosen from the group consisting of monoglyceride, diglyceride, fatty amide and fatty amide/glyceride mixture, wherein the fatty amide is in turn a reaction product of a fatty oil, monoglyceride, diglyceride or triglyceride, with an ethanolamine.

9. The process of claim 8, wherein the fatty acid derivative of an alcohol is chosen from the group consisting of glycerol monooleate, glycerol monostearate and fatty acid ethanolamide.

10. The process of claim 1, wherein the tungsten precursor is sodium tungstate dihydrate.

11. The process of claim 3, wherein in step (a)(i)(B), the acid is sulfuric acid.

12. The process of claim 1, wherein in step (b)(i)(A), the nitrogenous base is ethyldiisopropylamine.

13. The process of claim 1, wherein in step (b)(i)(A), the nitrogenous base is triethylamine.

14. A process for preparing a lubricating composition comprising, adding to a major amount of a lubricating base, an amount of organic tungsten complex prepared according to claim 1 to provide about 10 to 3000 ppm tungsten in the lubricating composition.

15. The process according to claim 14, wherein the amount of organic tungsten complex is added to provide about 10 to 1000 ppm tungsten.

16. The process according to claim 15, wherein the amount of organic tungsten complex is added to provide about 100 to 1000 ppm tungsten.

17. The process according to claim 16, wherein the amount of organic tungsten complex is added to provide about 700 ppm tungsten.

18. An organic tungsten complex formed as the reaction product of the process according to claim 1.

* * * * *